United States Patent [19]

Berger et al.

[11] 4,047,099
[45] Sept. 6, 1977

[54] METHOD AND APPARATUS FOR DETERMINING BOILER WATER CONDUCTIVITY

[75] Inventors: Lawrence A. Berger, Orange; Robert Carroll Hunt, Santa Ana, both of Calif.

[73] Assignee: Uniloc, Incorporated, Irvine, Calif.

[21] Appl. No.: 613,205

[22] Filed: Sept. 15, 1975

[51] Int. Cl.² .......................................... G01N 27/42
[52] U.S. Cl. .................................... 324/30 R; 324/118
[58] Field of Search ................. 324/30 R, 30 A, 78 J, 324/118

[56] References Cited

U.S. PATENT DOCUMENTS

| | | | |
|---|---|---|---|
| 3,368,144 | 2/1968 | Gerdes | 324/30 R |
| 3,430,130 | 2/1969 | Schneider | 324/30 R |
| 3,710,778 | 1/1973 | Cornelius | 324/30 R |
| 3,855,522 | 12/1974 | Kobayashi | 324/30 A |

Primary Examiner—Rudolph V. Rolinec
Assistant Examiner—Michael J. Tokar
Attorney, Agent, or Firm—Blakely, Sokoloff, Taylor & Zafman

[57] ABSTRACT

A method and apparatus for determining boiler water conductivity to minimize erratic readings due to the random presence of steam in the region of the conductivity sensor. The apparatus includes circuitry for providing a signal responsive to the peak conductivity detected by the sensor. This peak signal is stored in a storage circuit having a relatively slow decay rate so as to not be disturbed by subsequent lower and erratic conductivity probe signals, with the stored peak signals being updated by subsequent peak readings more indicative of the true conductivity of the water. An embodiment which steps to subsequent peak readings is also disclosed.

10 Claims, 4 Drawing Figures

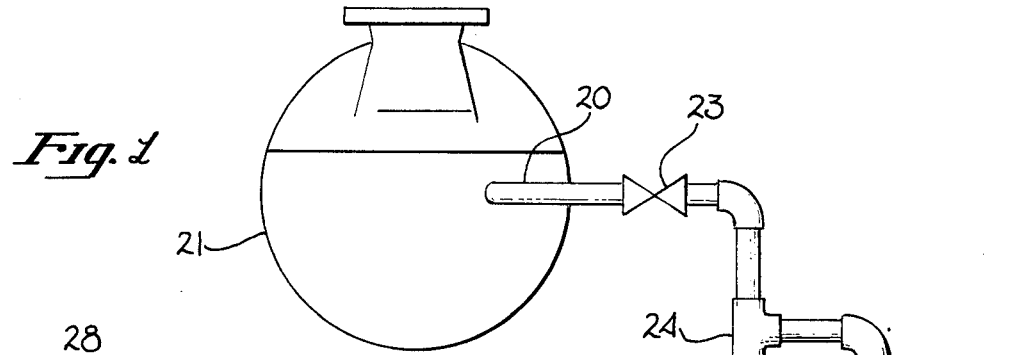
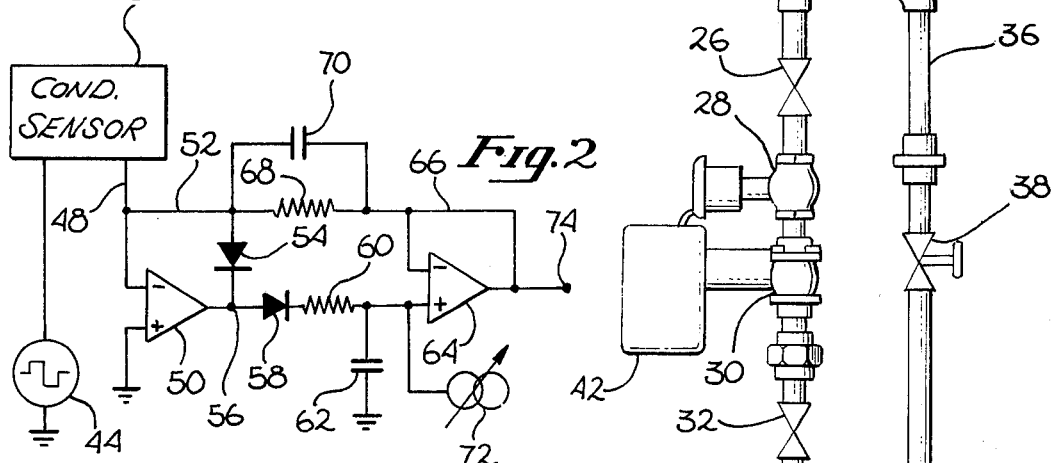
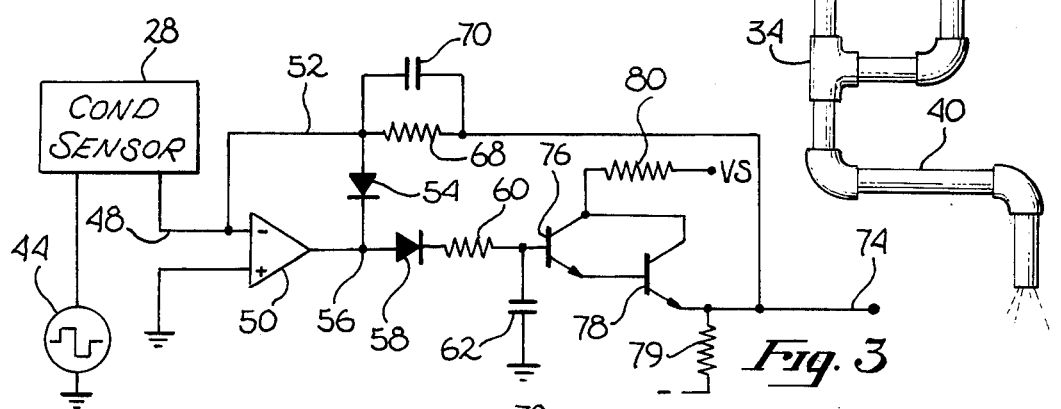
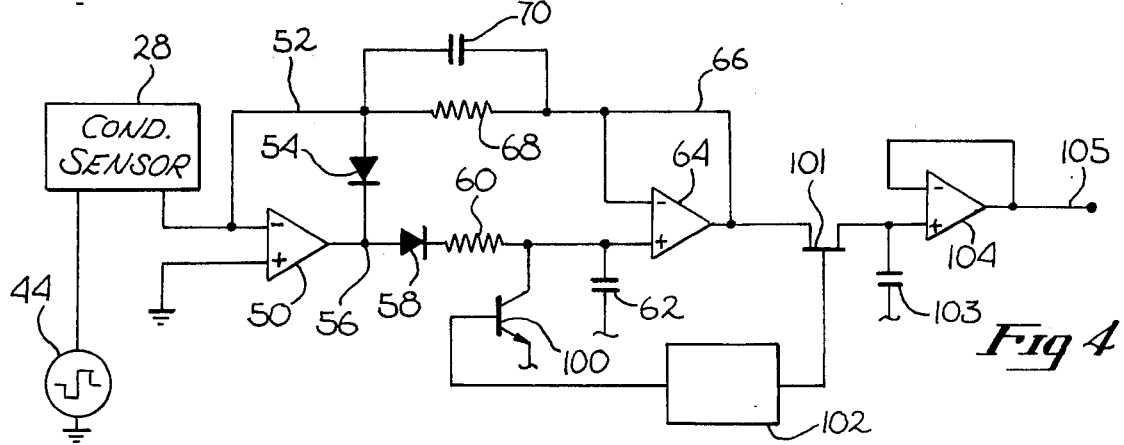

METHOD AND APPARATUS FOR DETERMINING BOILER WATER CONDUCTIVITY

BACKGROUND OF THE INVENTION

1. Field of the Invention

This invention relates to the field of boiler systems, and more particularly to devices and methods for providing substantially continuous measurement of water conductivity in a boiler.

2. Prior Art

In order to control the rate of build up of scale and other adverse effects in a boiler, it is a common practice to intermittently blowdown a boiler, that is, remove a portion of water therein and replace it with make-up water of lower mineral content and higher purity. The frequency with which this process must be carried out, however, will vary depending upon such factors as the boiler itself and its operating characteristics, and the purity and mineral content of the make-up water. Since the concentration of minerals, salts and other materials in the boiler water affect the electrical conductivity of the water, systems have been developed and are known in the prior art for providing blowdown valve control signals responsive in some form to the apparent conductivy of the boiling water.

One such prior art system is disclosed in U.S. Pat. No. 3,680,531 entitled "Automatic Boiler Blowdown Control." This patent discloses a specific location for the conductivity probe outside of the boiler region, chosen so as to minimize the entrained bubbles in the water flow around the probe. The patent also disclosed electronic circuitry to provide control signals and alarm signals responsive to the apparent conductivity of the water as sensed by the probe. In particular, in this system the probe is located in the blowdown line, and approximately every 15 minutes the blowdown valve is opened and an alternating signal is applied to the probe to provide the conductivity measurement. The blowdown valve is maintained in the open condition for so long as the apparent conductivity remains above a preset control valve, and is closed when the conductivity falls to the control point. Accordingly, if the apparent conductivity is below the control limit, the blowdown valve will close immediately after the conductivity reading is taken, whereas if the conductivity is above the control limit, the blowdown valve will remain open until the apparent conductivity is brought within the control value by the makeup water simultaneously being added to the boiler.

While the prior art systems attempt to minimize the presence of bubbles and flashing in the region of the probe, such adverse affects cannot be entirely eliminated. Accordingly, these systems have attempted to integrate the basic signal from the probe to provide an integrated or average signal in an attempt to minimize the erratic indications caused by the bubbles. However, the presence of bubbles and flashing in the region of the probe only reduces the apparent conductivity of the water. Therefore, the control signal derived by such systems is not responsive only to the conductivity of water, but instead is responsive to the conductivity of the boiler water as reduced by the frequency of occurence and the size of steam bubbles in the water.

BRIEF DESCRIPTION OF THE INVENTION

A method and apparatus for determining boiler water conductivity to minimize erratic readings due to the random presence of steam and other gaseous bubbles in the region of the conductivity sensor. The apparatus includes circuitry for providing a signal responsive to the peak conductivity detected by the sensor.

This peak signal is stored in a storage circuit having a relatively slow decay rate so as to not be disturbed by subsequent lower and erratic conductivity probe signals caused by the bubbles and steam pockets. The stored peak signals are updated by subsequent peak readings more indicative of the then true conductivity of the water, so that the output signal tracks the true conductivity of the boiler water within narrow limits. The time constant is the decay rate of the stored peak signals is preferably relatively long, being limited on the high end only by the slow rate of decrease of conductivity of the boiler water, and preferably being relatively long in comparison with the average time between accurate conductivity indications by the conductivity sensor so as to minimize the decay between accurate sensor outputs.

An alternate embodiment which steps to subsequent peak readings by sampling and storing is also described.

BRIEF DESCRIPTION OF THE DRAWINGS

FIG. 1 is a schematic representation illustrating a typical installation utilizing the present invention.

FIG. 2 is a schematic showing one embodiment of the present invention.

FIG. 3 is a schematic of the embodiment of FIG. 2 with a specific form of combined output amplifier and current sink.

FIG. 4 is a schematic of an alternate embodiment utilizing a sample and hold output.

DETAILED DESCRIPTION OF THE INVENTION

First, referring to FIG. 1, a schematic representation of a typical installation using the present invention may be seen.

A collector pipe 20 is normally disposed below the water level in the top drum 21 of the boiler, with a manual shutoff valve 23 being disposed in the collector pipeline close to the drum. The collector 20 is coupled through the valve 23 to a Tee 24 to split the flow into two possible flow paths. The first flow path is through a manual valve 26, past the conductivity sensor 28, the electrically controlled valve 30, and through another manual valve 32 to the combining Tee 34 and into the drainline 40.

The second flow path is through line 36 having a manual bypass valve 38 therein so as to provide manual blowdown control if desired. By using valves 26 and 32, the conductivity sensor 28 and/or the electrically operated valve 30 may be removed from the line of maintenance or repair if required, with the blowdown function being served temporarily with the manual bypass valve 38. The electrically operated valve 30 is controlled by the control 42, details of which will be described with respect to FIGS. 2 and 3.

Now referring to FIG. 2, a schematic of one form of the present invention may be seen. The purpose of this circuit is to provide a measurement of the conductivity of the water in the boiler to the highest accuracy possible, based upon fluctuating readings derived from the conductivity probe due to the presence of steam in the region of the probe. Such probes normally consist of a single electrode extending into the blowdown water flow area (See FIG. 1) with the blowdown pipe assembly forming the second electrode, so that the conduction of electrical current from one electrode to the other is an indication of the conductivity of the water in the blowdown system. Typically, the indications derived from such probes are quite erratic because of steam that may have been introduced into the collector pipe inside the drum or produced by flashing of the fast flowing fluid in the line itself. The presence of this steam, of course, reduces the conduction area between electrodes, resulting in rapid and repeated downscale fluctuations in the conductivity reading. Regardless of the mode of control of the blowdown valve or the type of final content element chosen, if this signal is used for adjustment of the element its action will become just as erratic as the reading. Such erratic response causes excessive wear of the control element and generally poor control. In some cases, the problem is so severe in the prior art systems that control is rendered impossible or at best unreliable. While averaging or integrating networks will produce a quieter signal, they still tend to detract from the accuracy of the system because of their significant reliance on measurements taken in the presence of stem (e.g., down-scale fluctuations only) which may vary not only on a short-term basis, but may generally drift over long periods. By way of sample, steam pick-up by the collector pipe 20 may vary from time to time based on variations within the boiler.

The present invention takes advantage of the fact that fluctuations in the readings of a conductivity probe are confined to the low side only. This is due to the fact that the presence of steam or bubbles in the blowdown fluid will decrease the conduction area and therefore can only decrease the apparent conductivity. There is no rebound or overshoot effect when the sensor is once again fully immersed in fluid. Thus, as the probe is completely surrounded by fluid, a valid conductivity reading will be obtained. Statistically, this has been found to occur in an average time of one to two seconds, with the rise in apparent conductivity to the correct value being roughly exponential. Because of the extremely slow rate of change of solids levels in any boiler drum, it is perfectly satisfactory to use this peak reading for control purposes even if it occurred on much less frequency intervals.

Thus, as shown in FIG. 2, a square wave oscillator 44 provides a square wave drive in the conductivity sensor 28, with the current in line 48 passed by the conductivity sensor 28 being applied to the negative input terminal of amplifier 50. Line 48 is also coupled through line 52 and diode 54 to the output 56 of amplifier 50, with the positive input of the amplifier being coupled to ground. With this connection, diode 54 provides direct feedback when the voltage on line 48 is positive (e.g., during the positive half of the square wave provided by the square wave oscillator 44). Thus, under this condition, the output provided by the amplifier 50 is clamped by the diode.

The output of amplifier 50 is coupled through a second didode 58 to an RC network comprising resistor 60 and capacitor 62. Diode 58 provides rectification of the output of amplifier 50 with capacitor 62, a relatively large capacitor, providing storage of the detected signal. Thus, if the sensor output represents a valid conductivity reading, capacitor 62 will be charged by amplifier 50 to a voltage indicative of that true reading, as determined by $R_{68}$ (the feedback resistor). The voltage across capacitor 62 (a positive voltage) is coupled to the positive input of amplifier 64, with the output thereof being coupled back through line 66 to the negative input of the amplifier. Thus, the feedback for amplifier 64 is maximized so that the gain of the amplifier is unity. The output voltage of amplifier 64 of course is of the output voltage V, indicative of the true conductivity of the water in the blowdown system (or in drum 22 if the conductivity probe is placed directly in the drum). The output voltage (line 66) is also coupled back through a network comprising resistor 68 and capacitor 70 to line 52. Also shown in FIG. 2 is a current sink 72, forming a small current drain of capacitor 62 so as to provide for the discharging thereof at a relatively long time constant (e.g., decay rate). If desired, the means for providing the discharging of capacitor 62 may be made adjustable to trim for optimum response and stability. In the embodiment of FIG. 2, the operational amplifier 64 may be adjusted so that the input offset current of the amplifier itself provides the desired current drain which in effect provides a decay rate rather than a true time constant characteristic. Suitable amplifiers with an input offset voltage adjustment include the National Semiconductor 301 operational amplifier. A resistor placed across the offset voltage (input terminals) will determine the current for the discharge rate, with the capability of adjusting the offset voltage automatically resulting in a variable discharge current.

The overall operation of the circuit of FIG. 2 when taking a conductivity measurement may be described as follows During the positive half cycle of the oscillator 44, current is provide into line 48 by the conductivity sensor 28 in accordance with the apparent conductivity of the water in the blowdown system. Thus, the voltage on line 48 is encouraged to a level higher than ground, whereas the output of amplifier 50 is encouraged to a voltage below ground. Accordingly, diode 54 is forward biased, thereby providing direct feedback to line 48. Since the open loop gain of amplifier 50 is high, this feedback holds the voltage on line 48 substantially at ground voltage. This phenomena results in a symmetrical drive on the probe 28, thereby preventing polarization. During the negative half cycle of oscillator 44, current is supplied through line 48 in the opposite direction into conductivity sensor 28, again in accordance with the apparent conductivity of the water surrounding the sensor. Accordingly, the voltage on line 48 is encouraged to a negative value and the output (point 56) of amplifier 50 is encouraged to a positive valve. This back-biases diode 54 and forward-biases diode 58 so as to charge storage capacitor 62. The resulting voltage on capacitor 62 is applied to the positive input of amplifier 64 with direct feedback of the amplifier output being applied to the negative input of the amplifier through line 66. This clamps the gain of amplifier 64 at unity (plus 1) so that the output voltage at point 74 is equal to the voltage on storage capacitor 62. This voltage is also fed back through the network comprised of resistor 68 and capacitor 70 to line 52 and the negative input to amplifier 50, thereby providing a feedback loop to amplifier 50. Resistor 68 is the gain determining resistor, and the output at terminal 74 is equal to the input voltage 44 times the product of the resistance of resistor 68 and the conductivity of the water.

It should be noted that this feedback loop for amplifier 50 during the negative half cycle of oscillator 44 provides for relatively fast charging of storage capacitor 62 to the peak level as indicated by the conductivity sensor. Thus, while capacitor 62 is charging, the voltage at point 56 will substantially exceed the steady state reading for the apparent conductivity then being sensed by the conductivity sensor, and in fact may temporarily go to saturation. However, the possibility of overshoot is substantially eliminated by the combination of resistor 68 and capacitor 70, since capacitor 70 provides a lead or stabilizing influence on the feedback, tending to cause the charging of capacitor 62 to the peak detected (negative) level on line 48 at a rate determined by the RC time constant of register 68 and capacitor 70, a time constant which in a preferred embodiment is on the order of 1 millisecond. Thus it may be seen that resistor 60 is a current limiting resistor for diode 58 and particularly amplifier 50, with the much shorter RC time constant of the feedback network minimizing the otherwise long time constant of the storage capacitor 62 and its charging network.

The current drain 72 provides one important aspect of the operation of the present invention. In particular the rate of discharge of capacitor 62 is obviously determined by the rate of withdrawal of current therefrom, which is schematically represented by the current drain. This discharge rate or equivalent time constant in the present invention should be at least greater than the rate of change of conductivity of the water in the boiler during blowdown so that the circuit may track the decrease in conductivity, but should be quite substantial in comparison to the statistical average time between true indications of the water conductivity, as sensed by the conductivity sensor 28, so as to provide minimal discharge between the reoccurrence of accurate readings. In this manner, the circuit will store an accurate or valid indication of water conductivity in capacitor 62, and will provide an output substantially equal to this previous accurate reading unit such time as an updated or new acurate reading is obtained. If, in the meantime however, the probe has been exposed to substantial proportions of steam, thereby grossly limiting the apparent conductivity, the output of the circuit will be insignificantly effected by such occurrence.

In a typical installation, the blowdown system will be sized so as to be capable of passing approximately twice the normal blowdown flow rate. Accordingly, a blowdown valve usually will operate with an approximately 50 percent duty cycle. Also, typically the blowdown flow rate is on the order of one quarter of the drum water per hour. Using these parameters, and further assuming that the conductivity is to be controlled within a 5 percent range (e.g., blowdown is to be initiated when conductivity drifts upward by approximately five percent), it can be shown that the blowdown time for a system having the foregoing parameters will be approximately 25 minutes. Also statistically, for a reasonably well-designed blowdown sytem wherein the physical arrangement and design of the components in the blowdown system are intended to minimize the presence of steam in the region of the probe, accurate or valid conductivity indications by the probe may be expected on the order of every 1 to 2 seconds. With these parameters, if the net current drain on capacitor 62 is such as to provide a discharge time constant for the capacitor of a few minutes, the output of the circuit at point 74 will be able to track the decreasing conductivity of the boiler water during blowdown, but at the same time will be substantially free of transient disturbances caused by erratic indications of the water conductivity by the conductivity sensor, regardless of the momentary amplitude of such erratic readings. While a time constant of 1 to 2 minutes is preferred, discharge time constants of as short as 10 seconds or as long as 10 minutes may be used. (Charging time constants should be short, however, preferably well under 1 second, and most preferably on the order of milliseconds.)

The current drain 72 on capacitor 62 may be take the form of a voltage independent current drain, a relatively high resistor to ground, or even to the finite input impedance of amplifier 64. In the preferred embodiment, amplifier 64 actually comprises a Darlington pair connected in an emitter follower configuration, with the base input current requirements for the first transistor of the pair providing the desired current drain, and with a load resistor 79 tied to a negative power supply terminal. Thus, as shown in FIG. 3, amplifier 64 is comprised of transistors 76 and 78 (and resistor 80) connected in a Darlington configuration, with the base of transistor 76 being coupled to the voltage on capacitor 62. Since line 48 is always substantially at ground voltage, resistor 68 represents a load on the output of the second transistor 78, and since the gain of the Darlington pair will fall within reasonable limits, the current drain provided by the base of transistor 76 will fall within the right order of magnitude and within reasonable limits, considering the fact that tight control of this discharge rate is not required.

The control 42 (FIG. 1) of which the circuit of FIG. 3 is part, opens the blowdown valve 30 in a cyclic manner through a conventional cycle duration timer having an adjustable cycle (ranging from every five minutes to every three hours in the preferred embodiment). The blowdown valve is held open for some predetermined duration which, in a preferred embodiment, is adjustable over the range of 10 seconds to 5 minutes. Even on the shorter duration time, however, of 10 seconds, an accurate reading of conductivity will be provided at the output of the circuit, which typically will exceed the maximum allowed conductivity by an amount within the control range. Accordingly, this signal is used to further control the valve, specifically maintaining the valve open until the conductivity in the boiler drops to the control point, whereupon the valve will be automatically closed by controller 42. The cycle duration timers will then reinitiate this control cycle at a subsequent time, dependent upon the adjustment thereof.

In the two embodiments heretofore described with respect to FIGS. 2 and 3, signals responsive to the peak conductivity of the water were derived and allowed to decay at a relatively slow rate until updated by subsequent accurate readings, either through a substantially constant decay rate caused by a fixed current drain, such as by way of example the input offset voltage of an operational amplifier, or caused by an exponential decay to a steady state level at a substantial time constant. As a further alternate, a particular peak value may be stored while subsequent peak values are being detected, and periodically updated with such subsequent readings. Such a system, shown in FIG. 4, will have an output characterized by step function decreases or increases in the output signal as opposed to a randomly updated decaying signal. Thus in FIG. 4, the input offset current for the amplifier 64 is held at a minimum so that capacitor 62, once charged, will have a negligible decay rate. Transistor 100 however will be used to dump the voltage on capacitor 62, with a second transistor 101 coupling the output of amplifier 64 to a second storage capacitor 103 and buffer output amplifier 104. A simple sequensor 102 is used to control transistor 100 and 101. In the steady state condition both transistors 100 and 101 are off. Periodically the sequensor turns on switch 101 for a very short period of charge capacitor 103; then switch 101 is turned off allowing the capacitor 103 to hold the sampled reading, and switch 100 is turned on momentarily to discharge capacitor 62. When transistor switch 100 is turned off, capacitor 62 is charged to a new peak responsive to the highest sensed conductivity prior to the next sampling cycle. The cycle is repeated at a rate set by the sequensor 102, which preferably is in the area of 30 seconds, but may reasonably range from approximately 10 seconds to five minutes. (If a ditigal output was desired, an A/D converter and a register may be coupled to line 105, and the signal used to turn on transistor 100 may be used to strobe the updated A/D converter output into the register.)

There has been described herein a blowdown control system, and more specifically a sub-system for providing maximum accuracy in the indication of conductivity of water in a boiler in spite of the presence of error sources such as steam and other gaseous bubbles in the presence of the conductivity probe. This system minimizes errors characteristic of prior art sensing systems by disregarding false indications of the conductivity probe through the detection and storage of the peak conductivity sensed by the probe. The stored signal is then updated with sufficient frequency, random or predetermined, to minimize the maximum error. While one specific embodiment has been disclosed and described in detail herein, it will be understood by those skilled in the art that various changes in form and detail may be made therein without departing from the spirit and scope of the invention.

We claim:

1. In a boiler system having a boiler water conductivity probe, an improved apparatus for providing a signal responsive to the conductivity of the boiler water with minimal regard to short term fluctuations due to the presence of steam bubbles or the like comprising:
   generating means coupled to a conductivity probe for providing an alternating first signal responsive to the apparent conductivity of the fluid surrounding the probe, said apparent conductivity being represented by short term fluctuations in said first signal;
   detecting means coupled to said conductivity probe and responsive to said first signal for providing second signals corresponding to the peak values of said first signal and not to the short term fluctuation in said first signal;
   storage means coupled to said detecting means for temporarily retaining said second signals; and,
   decay means for permitting said second signals retained by said storage means to decay at a decay rate selected to be greater than the corresponding rate of change of conductivity of the boiler water during blowdown and selected for minimal decay of said retained signals within the short term fluctuations between peak signals.

2. The improvement of claim 1 wherein the time constant of said predetermined decay rate is approximately 1 to 2 minutes.

3. In a boiler system, an improved apparatus for providing a signal responsive to the conductivity of the boiler water with minimal regard to short term fluctuations due to the presence of steam bubbles or the like comprising:
   a conductivity probe;
   means for applying an alternating signal to said probe;
   first amplifier means having its input coupled to said conductivity probe for providing a first signal comprising short term fluctuations responsive to the current through said probe;
   detection means coupled to the output of said first amplifier means for providing a DC voltage responsive to the peak level of said first signal and not to the short term fluctuations in said first signal;
   a storage capacitor coupled to said detection means for storing said DC voltage;
   means for allowing signals retained by said storage capacitor to decay at a rate selected to be greater than the corresponding rate of change of conductivity of the boiler water during blowdown and selected for minimal decay of said retained signals within the short term fluctuations between peak levels
   second amplifier means coupled to said storage capacitor for providing an output signal responsive to the voltage on said storage capacitor; and
   means for providing feedback of said output signal of said second amplifier means to the input of said first amplifier means to couple said first and second amplifiers and said detection means in a closed loop, thereby reducing the offset of said detection means by gain of said first amplifier means.

4. The improved apparatus of claim 3 wherein said means for providing feedback includes a lead network.

5. The apparatus of claim 1 wherein said generating means comprises a source of alternating voltage for coupling to a conductivity probe, and further including an amplifier means having an output coupled to said second means and an input for coupling to the conductivity probe, whereby said amplifier means is responsive to the current passing through said conductivity probe.

6. The apparatus of claim 5 further comprised of feedback means for coupling said retained signals back to the input of said amplifier means.

7. The apparatus of claim 1 wherein said decay means has a time constant of at least 10 seconds.

8. The apparatus of claim 1 wherein said decay means has a time constant ranging from 1 to 2 minutes.

9. The apparatus of claim 3 wherein said decay means has a time constant of at least 10 seconds.

10. The apparatus of claim 3 wherein said decay means has a time constant ranging from 1 to 2 minutes.

* * * * *

UNITED STATES PATENT OFFICE
CERTIFICATE OF CORRECTION

Patent No. 4,047,099  Dated September 6, 1977

Inventor(s) Lawrence A. Berger et al.

It is certified that error appears in the above-identified patent and that said Letters Patent are hereby corrected as shown below:

Column 1, line 26, "boiling" should be --boiler--.
Column 1, line 33, "disclosed" should be --discloses--.
Column 1, line 43, "valve" should be --value--.
Column 2, line 13, "is" should be --of--.
Column 2, line 54, "of" should be --for--.
Column 3, line 23, "stem" should be --steam--.
Column 3, line 46, "in" should be --to--.
Column 5, line 11, "of" should be --on--.
Column 4, line 35, "unit" should be --until--.
Column 5, line 59, "to" should be --or--.
Column 6, line 6, delete the word "be".
Column 6, line 8, delete the word "to".
Column 7, line 3, "of" should be --to--.

Signed and Sealed this

Twelfth Day of September 1978

[SEAL]

Attest:

RUTH C. MASON
*Attesting Officer*

DONALD W. BANNER
*Commissioner of Patents and Trademarks*